US006361292B1

(12) United States Patent
Chang et al.

(10) Patent No.: US 6,361,292 B1
(45) Date of Patent: Mar. 26, 2002

(54) LINEAR FLOW BLOOD PUMP

(76) Inventors: Sheldon S. L. Chang, P.O. Box 273, Port Jeff, NY (US) 11777; Andrew Chang, 4505 Harding Rd., #113, Nashville, TN (US) 37205

( * ) Notice: Subject to any disclaimer, the term of this patent is extended or adjusted under 35 U.S.C. 154(b) by 0 days.

(21) Appl. No.: 09/547,478

(22) Filed: Apr. 12, 2000

(51) Int. Cl.⁷ ............................ F04B 17/00; A61M 1/00
(52) U.S. Cl. ...................... 417/356; 417/410.4; 604/151
(58) Field of Search ............................ 417/356, 410.4; 418/48; 604/151

(56) References Cited

U.S. PATENT DOCUMENTS

| 1,892,217 A | | 12/1932 | Moineau | 222/372 |
| 3,479,960 A | * | 11/1969 | Cardoso | 103/117 |
| 4,482,305 A | * | 11/1984 | Natkai et al. | 418/48 |
| 4,802,827 A | * | 2/1989 | Fujiwara et al. | 417/356 |
| 5,588,812 A | | 12/1996 | Taylor et al. | 417/356 |
| 5,692,882 A | * | 12/1997 | Bozeman, Jr. et al. | 417/45 |
| 5,707,218 A | * | 1/1998 | Maher et al. | 417/356 |

OTHER PUBLICATIONS

Catanese, et al., "Outpatient Left Ventricular Assist Device Support: A Destination Rather Than a Bridge", Ann. Thoracic Surg., 62:646–53, 1996.

\* cited by examiner

Primary Examiner—Charles G. Freay
Assistant Examiner—Timothy P. Solak
(74) Attorney, Agent, or Firm—Hoffman & Baron, LLP

(57) ABSTRACT

The invention herein is a ventricular assistive device (VAD) based on a progressive cavity pump. A progressive cavity pump does not use blades or fins to propel the blood. Instead, the pump stator and rotor are designed so that, when combined, there are a series of cavities formed between the pump rotor and the stator wall. Blood is carried through the pump chamber in these cavities when the rotor rotates. In the preferred embodiment of the invention, the cavities progress on a straight line path through the pump, providing an efficient and unobstructed channel for blood flow and minimizing the risk of thrombus.

9 Claims, 2 Drawing Sheets

LINEAR FLOW BLOOD PUMP

BACKGROUND OF THE INVENTION

Ventricular assistive devices (VADs) are mechanical pumps that compensate for damaged or otherwise impaired hearts. They are used to restore normal hemodynamics and end-organ blood flow.

Early VADs closely emulated the pumping mechanism of the heart. Such devices provided a chamber which blood could be drawn into and then expelled out of. In the Thermo Cardiosystems pump, blood was drawn in and pushed out by means of a pusher plate mechanism. (Catanese et al., "Outpatient Left Ventricular Assist Device Support: A Destination Rather Than A Bridge," Ann. Thoracic Surg., 62:646–53, 1996.)

There are several problems with such devices. First, the only controllable quantity is the speed of the electric motor, which determines the number of pressure pulses per minute and the total volume of blood flow. Thus, it is not easy to tailor such devices for the needs of particular patients or particular circumstances. Second, the devices are inefficient, because the initial tendency of the pusher plate is to push the blood in all directions. Although the blood flow is eventually confined to only one direction by the action of the valves, it takes energy to actuate the output valve and to overcome the initially diffused motion.

A significant improvement in VADs is achieved by replacing impeller pumps with axial flow pumps, such as the Nimbus pump. (U.S. Pat. No. 5,588,812) Instead of using a pusher plate, axial flow pumps generally use blades or fins attached to a pump rotor to propel blood axially along a cylindrical conduit. However, blood has substantial viscosity and tends to also move radially with the propelling blades or fins. At a rotational speed of several thousand revolutions per minute, the centrifugal force cannot be ignored. As the centrifugally moving blood impinges against the walls of the cylindrical conduit, there is not only a loss of energy but also damage to the blood cells.

BRIEF SUMMARY OF THE INVENTION

The invention herein is a ventricular assistive device based on a progressive cavity pump. A progressive cavity pump does not use blades or fins to propel the blood. Instead, the pump stator and rotor are designed so that, when combined, there are a series of cavities formed between the pump rotor and the stator wall. Blood is carried through the pump chamber in these cavities when the rotor (or the rotor and stator both, as described below) rotates. In the preferred embodiment of the invention, the cavities progress on a straight line path through the pump, providing an unobstructed channel for blood flow and minimizing the risk of thrombus, i.e., blood clotting. Thus, the invention provides a more efficient mechanism for transporting blood that also reduces damage to the blood cells and reduces the risk of thrombus.

DETAILED DESCRIPTION OF THE INVENTION

Figure 1:
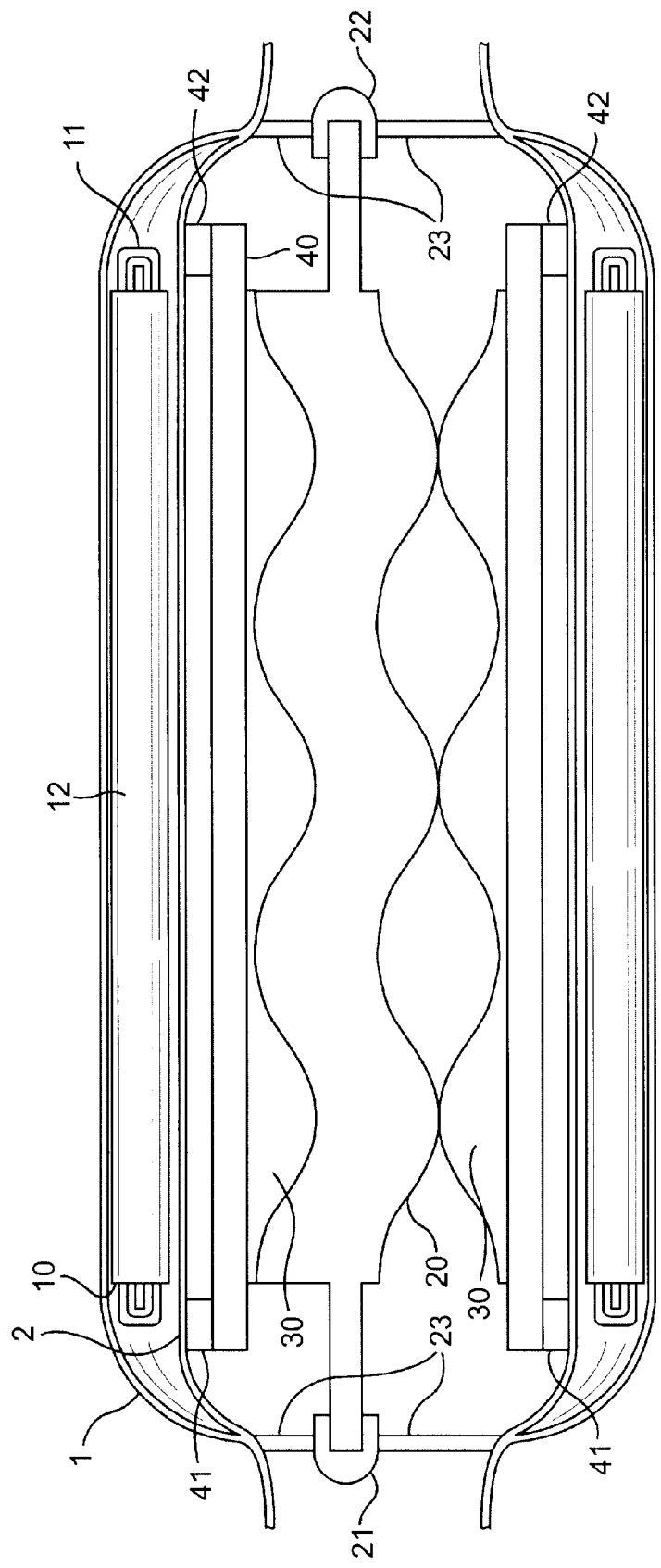
FIG. 1 shows a cross-section view of the linear flow blood pump of the invention.

The invention herein is a ventricular assistive device based on a progressive cavity pump. A progressive cavity pump does not use blades or fins to propel the blood. Instead, the pump stator and rotor are designed so that, when combined, there is a cavity or a series of cavities formed between the pump rotor and the stator wall. Blood is carried through the pump chamber in these cavities when the rotor (or the rotor and stator both, as described below) rotates.

I. The Progressing Cavity Pump

One embodiment of the invention uses a progressive cavity pump sometimes called a Moineau pump. (U.S. Pat. No. 1,892,217) In a conventional Moineau pump, the stator is stationary, while the rotor is driven to rotate around its own axis. The rotor is helical in shape, somewhat like a single-threaded screw. The rotor preferably has a circular cross-section of fixed diameter D, but may also take other shapes, such as elliptical. At each cross-section, the distance between the center of the cross-section and the rotor axis is E, the eccentricity of the pump. The rotor pitch $\rho_r$ is the length along the rotor axis required for one complete turn of the rotor thread.

The stator resembles a double-threaded screw, closely engaged with the rotor. Its cross-section is described by two semicircles of diameter D, connected by parallel sides of length 4E. The stator pitch $\rho_s$ is the length along the stator axis required for one complete turn of the stator thread. Since the stator is double-threaded, the stator pitch is twice the rotor pitch to enable the rotor and stator to engage properly: $\rho_s = 2\rho_r$.

As the rotor rotates, the stator causes the rotor axis to move in a circle of radius E around the stator axis, in the opposite direction and at the same speed ("counter-rotation"). At each cross-section, the rotor oscillates sinusoidally between the two extremes of the stator, i.e., between 2E and −2E, leaving empty spaces on each side of the rotor. (When the rotor cross-section is at either extreme, there is only one empty space. Otherwise there are two.) The empty spaces form sealed pockets, i.e., cavities, which transport the blood along a helical path through the pump. The cavities each extend a distance $\rho_s$ along the stator axis and wrap around the stator axis. The blood moves forward, i.e., axially, a distance $\rho_s$ for each revolution of the rotor.

The movement of the rotor and stator can be described mathematically as follows. The rotor can be completely described by the position r of the center of the circle at each cross-section z, where z is a coordinate along the pump axis. When the rotor is stationary:

$$r = E e^{jkz}$$

where $k = 2\pi/\rho_r$. Adding the rotation around the rotor axis, with n rotor revolutions per second, yields:

$$r = E e^{jkz} e^{-j\omega t} = E e^{j(kz - \omega t)}$$

where $\omega = 2\pi n$. Adding the counter-rotation around the stator axis yields:

$$r = E e^{j(kz - \omega t)} + E e^{-j\omega t} = \left[ 2E \cos\left(\frac{kz}{2} - \omega t\right) \right] e^{j\frac{kz}{2}} \quad (1)$$

The term in brackets shows that the movement of the rotor is sinusoidal, with an amplitude of displacement varying from −2E to 2E.

Because the rotor must be free to move in a circle around the stator axis, it cannot be connected directly to the motor. Instead, a connecting rod is used, permitting the rotor to move around the stator axis.

II. The Linear Flow Pump

Our preferred embodiment uses a variant of the Moineau pump. In this embodiment, both the rotor and the stator rotate, in the same direction, with the rotor rotating 2n revolutions per second, twice the speed of the stator, n revolutions per second. The rotor is thus rotating n revolutions per second relative to the stator. The stator rotation effectively eliminates any counter-rotation of the rotor. In other words, the rotor no longer moves in a circle around the stator axis. The rotor axis remains stationary at a fixed, parallel distance E from the stator axis.

The advantage of this mode of operation is that the blood travels on a straight path through the pump, rather than along a helical path. There is no radially directed blood flow. As a result, there is less damage to the blood cells because there is no centrifugal force driving the blood against the walls of the pump chamber. There is also a decreased probability that thrombus (blood-clotting) will occur inside the pump because the blood is flowing along a straight path.

The movement of the rotor and stator can be described as follows. Again, the rotor can be completely described by the position r of the center of the circle at each cross-section z, where z is a coordinate along the pump axis.

$$r = Ee^{j(kz-\omega t)} + E \quad (2)$$

where $\omega = 4\pi n$ because the rotor is rotating at 2n revolutions per second.

The rotor axis is parallel to the pump (stator) axis and located at a distance E from the pump axis. The rotor spiral has radius E and polar angle $\phi$:

$$\phi = kz - \omega t$$

Equation (2) can be rewritten $$r = E(e^{j\frac{\phi}{2}} + e^{-j\frac{\phi}{2}})e^{j\frac{\phi}{2}} = \left[2E\cos\frac{\phi}{2}\right]e^{j\frac{\phi}{2}} \quad (3)$$

showing that the rotor center at each cross-section moves with amplitude 2E along polar angle $\phi/2$.

The rotor moves inside the stator, so equation (3) also describes the stator. Thus, the stator is generated by a moving circle of diameter D with center at r. The bracketed term $$\left[2E\cos\frac{\phi}{2}\right]$$

shows that the stator is represented by a line of length 4E, centered on the pump axis.

The stator rotates at angular velocity $\omega/2$, i.e., half the rotor speed of rotation. For any given t, the stator cross-section rotates along the z axis at angular rate k/2. Since the stator is a line element of length 4E rotating about its center, it forms a double spiral long the z axis. The stator pitch $\rho_s$ is given by:

$$\frac{k}{2} = \frac{2\pi}{2\rho_r} = \frac{2\pi}{\rho_s}$$

Thus $\rho_s = 2\rho_r$, i.e., the stator pitch is twice the rotor pitch.

Fluid movement is compelled by the coupled rotation of the rotor and stator, represented by equations (2) and (3), respectively. As t increases by $\Delta t$ and z increases by $\Delta z$, where $$\Delta z = \frac{\omega}{k}\Delta t = 2n\rho_r\Delta t$$

there is no change in $\phi$ and, consequently, in equations (2) and (3). Thus, the trapped fluid is moved forward at a constant velocity $n\rho_s$ through the pump, and the volume of blood flow is given by:

$$V = 4DEn\rho_s$$

Either the stator or the rotor, or both, may be driven by the pump motor. An advantage of rotating the stator at half the speed of the rotor is that there is no need for a connecting rod, because the rotor axis remains fixed. In our preferred embodiment, only the stator is driven by the pump motor. The motor rotor is bonded to or integrated with the stator. (When "stator" and "rotor" are used alone, they refer to the pump stator and pump rotor, respectively. The terms "motor stator" and "motor rotor" are used to refer to the motor stator and motor rotor.) As the motor drives the stator, the rotor is forced to move in tandem, at twice the speed.

In our preferred embodiment, the motor operates by generating a rotating electromagnetic field. This can be done using a three-phase current, e.g., with a sinusoidal waveform (alternating current) or, more probably, with a square waveform (direct current). In FIG. 1, the motor stator 10 is secured to the pump housing 1, in the space between the pump housing 1 and the inner pump housing 2. The motor stator 10 is comprised of the motor stator windings 11 and the motor stator lamination 12. The motor stator 10 is outside the flow of blood. Other components of the invention, that come into contact with blood, are constructed of materials that are blood compatible.

The pump rotor 20 is supported by rotor bearings 21 and 22, each of which is secured to the pump housing 1 by a plurality of rotor bearing supports 23. The pump stator 30 is bonded to or integrated with the motor rotor 40. The motor rotor 40 is supported by motor rotor bearings 41 and 42, each of which is secured to the inner pump housing 2. The motor rotor bearings 41 and 42 should not permit blood cells to leak into the space between the motor rotor 40 and the inner pump housing 2. Otherwise, the outer surface of the motor rotor 40 may have fins, blades, grooves, or other structures (not shown) to promote blood flow in the space between the motor rotor 40 and the inner pump housing 2.

In most motors the stator windings are connected in series. As a result, if the motor rotor is displaced radially, the magnetic field in the direction of displacement is a stronger, tending to pull the motor rotor further in that direction. Consequently there is increased stress on the motor rotor bearings, which in this case could cause damage to blood cells. Therefore, in our preferred embodiment, the motor stator windings 11 are connected instead in parallel on opposite sides, with the result that the magnetic field does not tend to further displace the motor rotor 40 if it is displaced slightly radially.

The motor rotor 40 is preferably suitable for a synchronous motor, using permanent magnets, so that the motor rotor 40 follows the magnetic field generated by the motor stator 10 at the same speed of rotation. The pump stator 30 turns with the motor rotor 40, driving the pump rotor 20 at twice the speed. Other motor construction possibilities exist, e.g., synchronous reluctance motor with varying airgap, induction motor with a squirrel cage rotor, etc. Various motor designs are well-known to those of skill in the art, and the use of different motor designs to drive the pump of this invention is envisioned to be within the scope of this invention.

Figure 2:
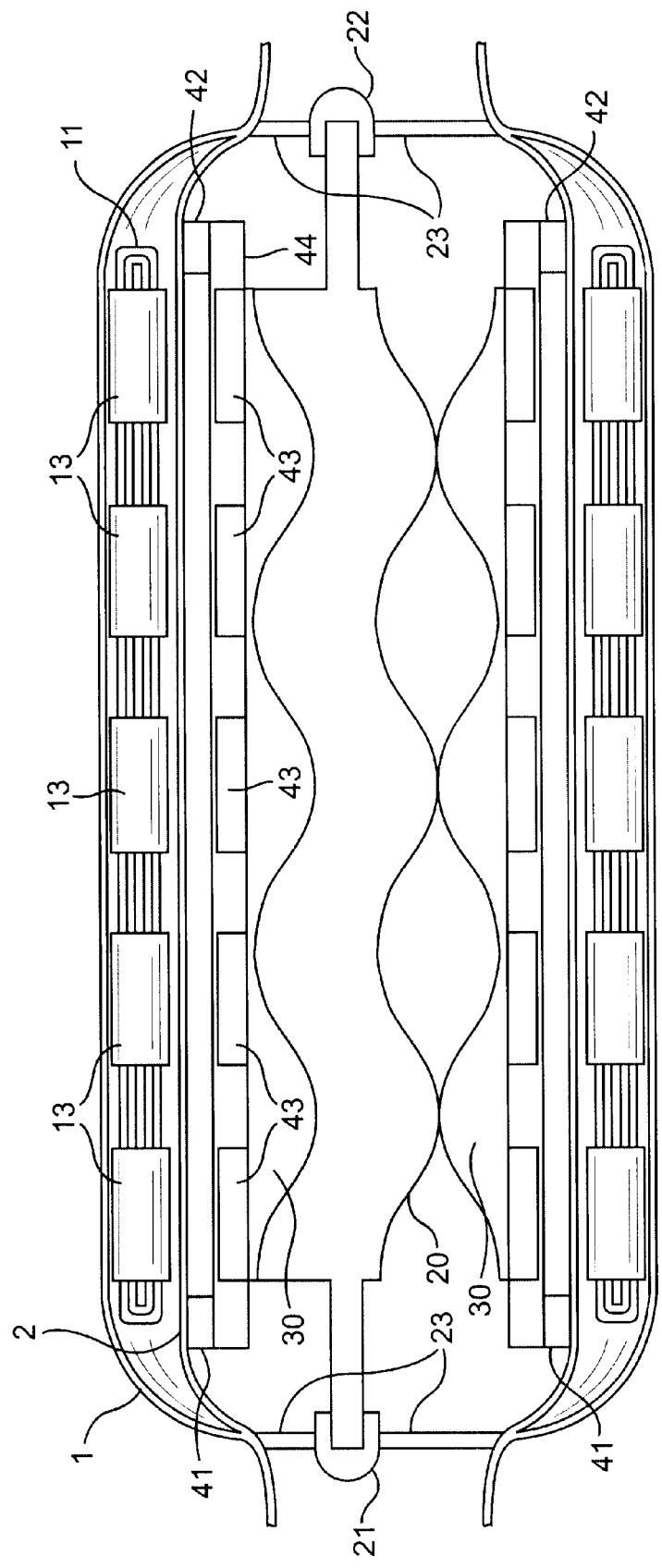
FIG. 2 shows a cross-section view of the linear flow blood pump of the invention using a segmented motor.

One improvement in motor design that is particularly useful in axial flow VADs is to segment the motor rotor and motor stator, as shown in FIG. 2. The purpose of this is to compensate for the reactive force on the pump rotor and pump stator as they carry blood through the pump. Otherwise, it may be necessary to use thrust bearings to keep the pump rotor and pump stator in place. The reactive force on the pump rotor and pump stator pushing against the direction of blood flow could then cause damage to the blood cells in the thrust bearings.

The effect of the segmented motor design is best appreciated by comparing FIG. 1 with FIG. 2. In FIG. 1, the motor rotor 40 is a cylindrical element set within a largely cylindrical motor stator 10. The motor stator 10 generates a rotating electromagnetic field, causing the motor rotor 40 within to rotate. As blood flows forward through the pump, the motor rotor 40 is forced backwards in reaction. However, as the motor rotor 40 is displaced axially, backwards, relative to the motor stator 10, the electromagnetic field pulls the motor rotor 40 forward. This compensating force occurs only at the edges of the electromagnetic field, i.e., only at the front and the back edges of the motor stator 10, and is therefore relatively weak.

In FIG. 2, the motor rotor and motor stator are segmented, and each segment of the motor stator generates an electromagnetic force operating on the corresponding segment of the motor rotor. Now when reactive force pushes the motor rotor backward, the electromagnetic field of each segment operates to pull the motor rotor forward, back into alignment, with much greater aggregate force. In FIG. 2, the motor rotor is comprised of multiple segments 43, each of which is a permanent magnet, and an outer sleeve 44, which holds the segments 43 in place. The motor stator is comprised of the stator windings 11 and the multiple segments 13 of the motor stator lamination.

A pressure pulse in the direction of flow can be produced by a sharp increase in the magnitude of the motor currents followed by a more gradual increase in the frequency of the motor currents. Likewise, a pressure pulse against the direction of flow can be produced by a sharp decrease in the magnitude of the motor currents followed by a more gradual decrease in the frequency of the motor currents. A gradual change in flow volume without an accompanying pressure pulse is accomplished by gradually changing the frequency of the motor currents. Thus, the timing, magnitude and direction of pressure pulses and the flow volume can be independently controlled.

We claim:

1. An axial flow blood pump, comprising:
   a pump stator, a pump rotor positioned within said pump stator, and drive means for driving one of said pump stator and said pump rotor, wherein said drive means comprises a motor including a motor stator and a motor rotor, said motor stator including at least a pair of windings, wherein the at least two windings arranged on physically opposite sides of the motor stator are connected in parallel to reduce unbalanced magnetic forces, and wherein said pump stator and said pump rotor rotate together to form a plurality of cavities, said cavities carrying blood forward through said pump as said motor drives one of said pump stator and pump rotor.

2. An axial flow blood pump as claimed in claim 1, wherein said cavities progress in a straight line path through the pump.

3. An axial flow blood pump, comprising:
   a pump stator, a pump rotor positioned within said pump stator, and drive means for driving at least one of said pump stator and pump rotor, wherein said drive means comprises a motor having a motor stator and a motor rotor, said motor stator comprises longitudinally spaced segments and said motor rotor is correspondingly segmented, and further wherein said pump stator and said pump rotor together form a plurality of cavities, said cavities carrying blood forward through said pump as said motor drives at least one of said pump stator and pump rotor.

4. A method of pumping blood comprising the steps of:
   providing an axial flow pump which includes an inlet and an outlet;
   a pump rotor mounted within a pump stator and drive means for rotating at least one of said pump stator and said pump rotor;
   rotating said pump stator and pump rotor together thereby forming a plurality of moving cavities therebetween; and
   carrying blood from said inlet to said outlet via the moving cavities formed by the pump stator and pump rotor.

5. A method as defined in claim 4, wherein the drive means is a motor and the motor rotates the pump stator.

6. A method as defined in claim 5, wherein the motor comprises a motor stator and a motor rotor and the motor rotor and the pump stator are fixedly attached.

7. A method as defined in claim 6, wherein the pump stator is in the form of a double-threaded screw.

8. A method as defined in claim 6, wherein the motor stator includes windings and said windings on physically opposite sides of the motor stator are connected in parallel.

9. A method as defined in claim 4, wherein the drive means comprises a motor, the motor including a motor stator and a motor rotor, the motor stator including longitudinally spaced segments and said motor rotor is correspondingly segmented.

* * * * *